(12) United States Patent
Knauf et al.

(10) Patent No.: US 10,364,214 B1
(45) Date of Patent: Jul. 30, 2019

(54) METHOD FOR PRODUCING ISOCYANATES

(71) Applicant: Covestro Deutschland AG, Leverkusen (DE)

(72) Inventors: Thomas Knauf, Dormagen (DE); Dirk Manzel, Moers (DE); Peter Plathen, Krefeld (DE); Jürgen Spriewald, Kölln-Reisiek (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/327,443

(22) PCT Filed: Aug. 29, 2017

(86) PCT No.: PCT/EP2017/071602
§ 371 (c)(1),
(2) Date: Feb. 22, 2019

(87) PCT Pub. No.: WO2018/041799
PCT Pub. Date: Mar. 8, 2018

(30) Foreign Application Priority Data

Sep. 1, 2016 (EP) ..................................... 16186777

(51) Int. Cl.
*C07C 263/10* (2006.01)
(52) U.S. Cl.
CPC .................................. *C07C 263/10* (2013.01)
(58) Field of Classification Search
CPC .................................................... C07C 263/10

USPC ......................................................... 558/342
See application file for complete search history.

(56) References Cited

U.S. PATENT DOCUMENTS

| | | |
|---|---|---|
| 4,764,308 A | 8/1988 | Sauer et al. |
| 4,851,570 A | 7/1989 | Zaby et al. |
| 5,599,968 A | 2/1997 | Bankwitz et al. |
| 6,974,880 B2 | 12/2005 | Biskup et al. |
| 7,118,653 B2 | 10/2006 | Brady et al. |
| 7,442,835 B2 | 10/2008 | Keggenhoff et al. |
| 7,547,801 B2 | 6/2009 | Pohl et al. |
| 7,584,629 B2 | 9/2009 | Sohn et al. |
| 7,645,900 B2 | 1/2010 | Lorenz et al. |
| 7,649,108 B2 | 1/2010 | Schal et al. |
| 8,079,752 B2 | 12/2011 | Rausch et al. |
| 8,097,751 B2 | 1/2012 | Koch et al. |
| 9,024,057 B2 | 5/2015 | Biskup et al. |
| 9,840,461 B2 | 12/2017 | Knauf et al. |
| 2006/0001146 A1 | 1/2006 | Sohn et al. |
| 2006/0123842 A1 | 6/2006 | Sohn et al. |
| 2007/0261437 A1 | 11/2007 | Boonstra et al. |
| 2010/0298596 A1 | 11/2010 | Keggenhoff et al. |

*Primary Examiner* — Kristin A Vajda
(74) *Attorney, Agent, or Firm* — Donald R. Palladino

(57) ABSTRACT

The invention relates to a method for producing isocyanates, according to which exhaust flows provided for the combustion are guided through an adsorption device before being supplied into the exhaust gas combustion process, and are thereby depleted of solvent, the adsorption device comprising at least two adsorption units connected in parallel, which are alternately (i) exposed to the at least one exhaust flow and (ii) regenerated with water vapor, where, during method step (i), an exhaust flow depleted of solvent is obtained, and during method step (ii), a flow containing water and solvent is obtained, the solvent proportion of which is recycled into a method for producing isocyanates.

15 Claims, 2 Drawing Sheets

METHOD FOR PRODUCING ISOCYANATES

CROSS REFERENCE TO RELATED APPLICATION

This application is a national stage application under 35 U.S.C. § 371 of PCT/EP2017/071602, filed Aug. 29, 2017, which claims the benefit of European Application No. 16186777.5, filed on Sep. 1, 2016, each of which being incorporated by reference herein.

FIELD

The present invention relates to a process for preparing isocyanates, in which offgas streams intended for combustion, before being sent to the offgas combustion, are guided through an adsorption apparatus and, in this way, are depleted of solvent, wherein the adsorption apparatus comprises at least two adsorption units connected in parallel that are alternately
 (i) charged with the at least one offgas stream and
 (ii) regenerated with steam,
wherein, during process stage (i), a solvent-depleted offgas stream is obtained and, during process stage (ii), a stream comprising water and solvent is obtained, the solvent fraction of which is recycled into the process for preparing isocyanates.

BACKGROUND

In many industrial production processes, especially production processes for chemical products, gaseous process products other than the actual product of the production process are obtained, which, before they are released as offgases into the environment, have to be processed in order to minimize economic losses and damage to the environment. Such workup steps may include various processes. Examples of such cleaning operations include scrubbing, absorption (for example of $NO_x$), adsorption, condensation and filtration. It is customary in the prior art to combine such gaseous process products that have been subjected to preliminary cleaning in this way on conclusion of all cleaning operations conducted for preliminary cleaning (and possibly even beforehand) and to send the offgas stream thus obtained to a common offgas combustion in which the offgas is combusted sufficiently completely that the combustion gases (if required after further cleaning, for example a base scrubbing to bind acidic constituents) can be released into the environment while complying with official environmental regulations.

One example of an industrial production process in which gaseous process products are obtained is the production of isocyanates by phosgenation of the corresponding amines. In the phosgenation, a gaseous process stream comprising the hydrogen chloride co-product and unconverted phosgene is obtained. Residues of the solvent used (and also inerts or else excess carbon monoxide from the phosgene preparation) are regularly also present therein. Workup steps that follow may give further gaseous process products, some of which also contain solvent. In this connection, the recovery of solvent from the various gaseous process products obtained at different points in the process is important. Processes for solvent recovery via distillation in isocyanate production processes are addressed, for example, by EP 1 575 908 B2 and EP 1 575 906 B1. None of these publications describes solvent recovery immediately prior to the offgas combustion.

WO 2004/056758 A1 describes further purification of hydrogen chloride from hydrogen chloride/phosgene separation by adsorption of impurities (residues of phosgene and chlorobenzene) on activated carbon.

It would be desirable to have a reliable process available for solvent recovery from offgas streams from isocyanate production plants before introduction thereof into the offgas combustion.

It would also be desirable to be able to adapt such a process in a simple manner to altered boundary conditions, for example altered costs for solvent, energy or offgas combustion.

SUMMARY

Taking account of this requirement, the present invention provides a process for preparing an isocyanate (1), comprising the steps of:
 A. reacting the amine (2) that corresponds to the isocyanate (1) with phosgene (3) using a solvent (4) to obtain a liquid stream comprising the isocyanate (1) and solvent (4) and at least one solvent-containing offgas stream;
 B. working up the liquid stream comprising isocyanate and solvent to isolate the isocyanate, wherein further solvent (4) may be used and wherein at least one solvent-containing offgas stream is likewise obtained;
wherein
 a) the at least one solvent-containing offgas stream from step A and/or from step B is guided into an adsorption apparatus for adsorption of solvent (3020) comprising at least two adsorption units (3021, 3022) connected in parallel that are alternately
  (i) charged with the at least one offgas stream and
  (ii) regenerated with steam,
  wherein, during process stage a) (i), a solvent-depleted offgas stream (220) is obtained and, during process stage a) (ii), a stream comprising water and solvent (230) is obtained, wherein
 b) (i) the solvent-depleted offgas stream (220) is sent to an offgas combustion (6000) and
  (ii) the stream comprising water and solvent (230) is depleted of water and then recycled into step A and/or into step B.

The present invention further provides a plant (10 000), suitable for performance of the process according to the invention, for preparing an isocyanate (1) by phosgenation of the corresponding amine (2).

There follows firstly a brief summary of various possible embodiments of the invention:

In a first embodiment of the invention, which may be combined with all other embodiments, step A comprises:
 I) reacting the amine (2) with phosgene (3) and separating the process product obtained into the liquid stream (60) comprising the isocyanate and solvent, and a gaseous stream (70) comprising phosgene, hydrogen chloride and solvent;
and step B comprises:
 II) depleting phosgene and hydrogen chloride from the liquid stream (60) from step I) by separating this liquid stream (60) into a liquid stream (80) comprising solvent and isocyanate, and a gaseous stream (90) comprising phosgene and hydrogen chloride in a distillation apparatus (2100);
wherein the gaseous streams (70) and (90), optionally after passing through further cleaning steps, are sent to step a) as a constituent, if appropriate as the sole constituent, of the at least one solvent-containing offgas stream.

In a second embodiment of the invention, which is a particular configuration of the first embodiment, step B.II) is followed by steps B.III) and B.IV):

III) depleting solvent from the liquid stream (80) from step II) by separating this liquid stream (80) into a gaseous stream (110) comprising solvent, and a liquid stream (100) comprising isocyanate in a distillation apparatus (2200);

IV) depleting phosgene from the gaseous stream (110) from step IV) by separating this gaseous stream (110), preferably after its liquefaction in a condenser (2310), into a liquid stream (120) comprising solvent and a gaseous stream (130) comprising phosgene in a distillation apparatus (2300);

wherein the gaseous stream (130), optionally after passing through further cleaning steps, is sent to step a) as a constituent of the at least one solvent-containing offgas stream.

In a third embodiment of the invention, which is a particular configuration of the second embodiment, step B.IV) is followed by:

V) obtaining a liquid isocyanate stream (140) from the liquid stream (100), resulting in a gaseous stream (150) comprising secondary components and optionally solvent, in a distillation apparatus (2400), optionally comprising the removal of polymeric isocyanate fractions in an upstream unit for polymer removal (2410) as stream (141).

In a fourth embodiment of the invention, which is a particular configuration of the first, second and third embodiments, step B additionally comprises:

VI) cleaning the gaseous streams (70) and (90) and, if present, the gaseous stream (130), optionally after condensation, by absorption in solvent (4) to obtain a liquid stream (160) comprising solvent and phosgene, and a gaseous stream (170) comprising hydrogen chloride and solvent in an absorption apparatus (2500).

In a fifth embodiment of the invention, which is a particular configuration of the fourth embodiment, step B.VI) is followed by:

VII) cleaning the gaseous stream (170) in water or hydrochloric acid as absorbent (180) in a further absorption apparatus (2600) to obtain a hydrochloric acid-containing stream (190) and, preferably after passing through a vapor condenser (2610), a gaseous stream (200) comprising solvent and optionally gaseous secondary components.

In a sixth embodiment of the invention, which is a particular configuration of the fifth embodiment, step B.VII) includes passage through the vapor condenser (2610), and this step B.VII) additionally comprises the following:

separating the liquid stream (191) obtained in the vapor condenser (2610) into an aqueous phase (192) and an organic phase (193);

recycling the aqueous phase (192) as a constituent of the absorbent (180) into the absorption apparatus (2600) and/or recycling the organic phase (193), preferably after drying, into at least one of steps A.I), B.III), B.IV and B.VI).

In a seventh embodiment of the invention, which is a particular configuration of the fifth and sixth embodiments, step B.VII) is followed by:

VIII) cleaning the gaseous stream (200) comprising solvent and optionally gaseous secondary components in an apparatus for workup of offgas streams (3000), wherein VIII-1) the gaseous stream (200) that originates from the absorption apparatus (2600), preferably after passing through the vapor condenser (2610), is guided into an apparatus for phosgene decomposition (3010) in which phosgene is broken down catalytically, preferably over activated carbon, using water (260) to obtain a gaseous stream (210) comprising solvent and optionally gaseous secondary components and a liquid stream (270) comprising hydrochloric acid, wherein the gaseous stream (210) is guided into the adsorption apparatus (3020) for adsorption of solvent in step a).

In an eighth embodiment of the invention, which is combinable with all other embodiments of the invention, especially with the seventh embodiment, the phosgene (3) for the performance of step A is prepared by reacting carbon monoxide (300) with chlorine (310), giving an offgas stream (320) comprising carbon monoxide and phosgene which, optionally after passing through further cleaning steps, is fed into the at least one solvent-containing offgas stream to be sent to the offgas combustion, more particularly in such a way that the offgas stream (320), optionally after passing through further purification steps, is combined with the gaseous stream (200) prior to performance of step VIII.1).

In a ninth embodiment of the invention, which is a particular configuration of the eighth embodiment, the offgas stream (320) comprising carbon monoxide and phosgene from the reaction of carbon monoxide (300) with chlorine (310) is cleaned in solvent (4) having a temperature in the range from 0.0° C. to −20.0° C. in an absorption column (4010) to give a phosgene-depleted offgas stream (330), wherein this offgas stream (330), prior to performance of step VIII.1), is combined with the gaseous stream (200), giving a solvent- and phosgene-containing stream (340) in the absorption column (4010) which is sent to the absorption apparatus (2500).

In a tenth embodiment of the invention, which is combinable with all other embodiments of the invention, especially with the fourth, fifth, sixth, seventh, eighth or ninth embodiment, the depletion of water from the stream comprising water and solvent in step b) (ii) is conducted in such a way that this stream is condensed and then separated into an aqueous phase (250) and an organic phase (240), wherein the organic phase (240) may optionally be dried further, wherein the recycling of the stream obtained after depletion of water into step A and/or into step B is conducted in such a way that the organic phase (240), optionally after further drying, is recycled into step A and/or into step B, more particularly into at least one of steps A I), B.III), B.IV) and B.VI).

In an eleventh embodiment of the invention, which is a particular configuration of the tenth embodiment, the aqueous phase (250) is used as a constituent of the absorbent used in step B.VII).

In a twelfth embodiment of the invention, which is a particular configuration of the second to eleventh embodiments, especially of the third to eleventh embodiments, the units (2200) and (2300), especially the units (2200), (2300), (2400) and, if present, (2410) are operated at a reduced pressure relative to atmospheric pressure and the offgas streams from the vacuum generation plants that are required for this purpose are sent to step a) without cooling or after cooling to a temperature not lower than 1.0° C., optionally after passing through an apparatus for catalytic phosgene decomposition (3010).

In a thirteenth embodiment of the invention, which may be combined with all other embodiments, the amine (2) is selected from the group consisting of methylene diphenylene diamine, polymethylene polyphenylene polyamine, a mixture of methylene diphenylene diamine and polymethylene polyphenylene polyamine, tolylenediamine, xylylenediamine, pentane-1,5-diamine, hexamethylenediamine, isophoronediamine and naphthyldiamine. Preferably, the amine is selected from the group consisting of methylene diphenylene diamine, polymethylene polyphenylene polyamine, a mixture of methylene diphenylene diamine and polymethylene polyphenylene polyamine, tolylenediamine, xylylenediamine, hexamethylenediamine, isophoronediamine and naphthyldiamine.

DETAILED DESCRIPTION

Figure 1:
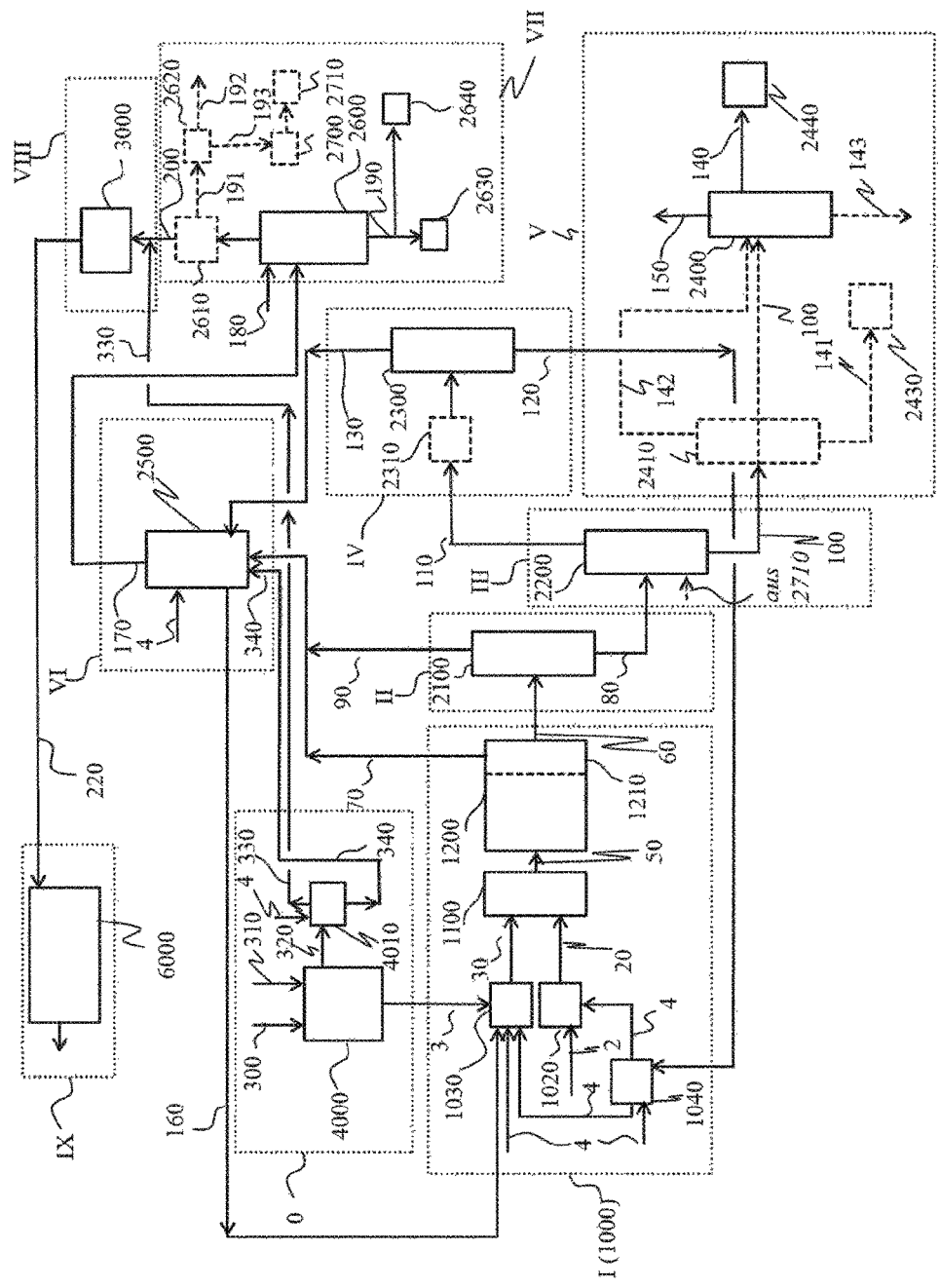
FIG. 1 is a schematic diagram of a plant for preparation of an isocyanate by phosgenation of the corresponding amine.

The embodiments briefly outlined above and further possible configurations of the invention are elucidated in detail hereinafter. Various embodiments are combinable with one another as desired unless the opposite is apparent to the person skilled in the art from the context.

The process of the invention is suitable in principle for preparation of any desired aromatic, aliphatic and araliphatic isocyanates (1). Preference is given to using the process of the invention for preparation of methylene diphenylene diisocyanate (from methylene diphenylene diamine), polymethylene polyphenylene polyisocyanate (from polymethylene polyphenylene polyamine), mixtures of methylene diphenylene diisocyanate and polymethylene polyphenylene polyisocyanate, tolylene diisocyanate (from tolylenediamine), xylylene diisocyanate (from xylylenediamine), pentane 1,5-diisocyanate (from pentane-1,5-diamine), hexamethylene diisocyanate (from hexamethylenediamine), isophorone diisocyanate (from isophoronediamine) and naphthyl diisocyanate (from naphthyldiamine), more preferably of methylene diphenylene diisocyanate, mixtures of methylene diphenylene diisocyanate and polymethylene polyphenylene polyisocyanate, and tolylene diisocyanate. The process of the invention is most preferably suitable for preparation of methylene diphenylene diisocyanate and mixtures of methylene diphenylene diisocyanate and polymethylene polyphenylene polyisocyanate. Methylene diphenylene diisocyanate is also referred to as the diamine of the diphenylmethane series. Polymethylene polyphenylene polyisocyanate is also referred to as the polyamine of the diphenylmethane series.

Step A can be effected in the gas phase or liquid phase. In liquid phase phosgenations, it is customary to dissolve and react amine (2) and phosgene (3) in a solvent (4). In gas phase phosgenations, it is customary to rapidly cool the crude gaseous process product from the reaction of amine and phosgene by contacting with solvent (4) (and optionally further liquid such as recycled isocyanate) at a temperature below the boiling point of the isocyanate (1) and above the decomposition point of the corresponding carbamoyl chloride, with conversion of the isocyanate formed to the liquid phase that forms. Irrespective of the process regime, what is thus formed is a liquid stream comprising the isocyanate (1) and solvent (4). There is always additional formation of gaseous process products that are subjected to further workup, with the greatest possible extent of recovery of valuable raw materials. After exhaustion of the means of workup of the gaseous process products that are possible and economically viable in the prior art to date, there always remain offgas streams. Since the complete recovery of solvent from all gaseous process products would be uneconomic owing to the disproportionately high energy input required for the purpose, at least one solvent-containing offgas stream is regularly obtained in a process for preparing isocyanates. According to the invention, this at least one solvent-containing offgas stream, prior to the offgas combustion (step b) (i)), is further depleted of solvent by an adsorption process (step a)). It is preferable here that this depletion of solvent takes place immediately before the offgas combustion, i.e. there are preferably no further process steps that take place between step a) and step b) (i).

Suitable inert solvents (4) usable in accordance with the invention are solvents that are inert under the reaction conditions, for example monochlorobenzene, dichlorobenzene (especially the ortho isomer), dioxane, toluene, xylene, methylene chloride, perchloroethylene, trichlorofluoromethane or butyl acetate. The inert solvent (4) is preferably essentially free of isocyanate (target proportion by mass <100 ppm) and essentially free of phosgene (target proportion by mass <100 ppm), and this should be noted when using recycling streams. Preference is therefore given to working by a process as described in EP 1 854 783 A2. The solvents can be used individually or in the form of any desired mixtures of the solvents mentioned by way of example. Preference is given to using monochlorobenzene (MCB) or ortho-dichlorobenzene (ODB).

In the context of the present invention, step B can be conducted as customary in the prior art. Preferred embodiments are outlined further down.

Step a) of the process according to the invention comprises the depletion of solvent from the at least one solvent-containing offgas stream to be combusted in an adsorption apparatus for adsorption of solvent. This comprises at least two adsorption units connected in parallel, comprising an adsorbent (preferably activated carbon). One of these adsorption units is charged in a) (i) with the at least one solvent-containing offgas stream which is subsequently to be combusted, at most up to the saturation limit of the adsorbent. Then the at least one solvent-containing offgas stream to be combusted, in a) (ii), is guided into the second adsorption unit comprising fresh or regenerated adsorbent, and at the same time the adsorbent contained in the first adsorption unit is regenerated with steam. Preferred configurations of step a) are elucidated in detail further down.

In step b) (i), the solvent-depleted offgas stream (220) is preferably fed directly to an offgas combustion (i.e. preferably without intermediate steps between step a) (i) and b) (i)). The offgas combustion is a step known to the person skilled in the art in chemical engineering and, in the context of the present invention, can be conducted as customary in the prior art.

The depletion of water from the stream comprising water and solvent which is obtained in step a) ii), in step b) (ii), is appropriately conducted in such a way that this stream is condensed and then separated into an aqueous phase and an organic phase, wherein the organic phase may optionally be dried further, and in which the recycling of the stream obtained after depletion of water into step A and/or into step B is conducted in such a way that the organic phase, optionally after further drying, is used as a constituent of the solvent (4) in step A and/or in step B. Preferred configurations of this step are elucidated in detail further down.

There follows a detailed description with reference to the appended drawings, where different embodiments are again combinable with one another as desired unless the opposite is apparent to the person skilled in the art from the context.

The continuous or semicontinuous, preferably continuous, production of the isocyanate in step A is effected by a process known from the prior art. Suitable processes are described, for example, in EP 2 077 150 A1, EP 1 616 857 A1, EP 1 873 142 A1, EP 0 716 079 A1 and EP 0 314 985 B1 (liquid phase processes), and EP 2 196 455 A1, EP 1 449 826 A1 and WO 2015/144681 A1 (gas phase processes). However, concentrations and flow rates of the amine (2) and phosgene (3) reactants are preferably chosen such that a molar ratio of phosgene to primary amino groups of 1.1:1 to 30:1, more preferably of 1.25:1 to 3:1, is established in the mixing of the co-reactants.

In a preferred embodiment of the process according to the invention, step A comprises:
  I) reacting the amine (2) with phosgene (3) and separating the process product obtained into the liquid stream (60) comprising the isocyanate and solvent, and a gaseous stream (70) comprising phosgene, hydrogen chloride and solvent.

Amine (2) and phosgene (3) are fed to the mixing in (1100) from corresponding reservoir vessels (1020, 1030) (see FIG. 1). This is preferably done in the form of solutions (20, 30) in the solvent (4). In the case of gas phase processes, it is possible to dispense with the dissolution of the reactants in solvent (4). Suitable mixing units 1100 are sufficiently well known from the prior art. After the mixing, the reaction mixture (50) is guided into the reaction space (1200). This is a dwell time unit in which the mixture obtained in the mixing unit 1100 is given sufficient opportunity to react to completion. Suitable apparatuses are sufficiently well known from the prior art. The separation of the crude process product into liquid stream 60 and the gaseous stream 70 is effected in the reaction space itself or in a downstream separator unit 1210. It is also possible to integrate the mixing unit and the reaction space or the mixing unit, the reaction space and the separator unit or the reaction space and the separator unit in a single apparatus (for example in a corresponding reactor). According to the invention, it is also possible for multiple mixing units and/or reaction spaces and/or, if present, separator apparatuses to be connected in series or in parallel; for example in the form of a cascade of multiple series-connected reactors. The process product obtained in 1200 separates into a liquid phase (60) comprising, as well as the desired isocyanate, dissolved hydrogen chloride, excess dissolved phosgene and solvent, and a gas phase (70) comprising hydrogen chloride gas, excess gaseous phosgene and gaseous solvent. Liquid phase and gas phase are removed separately from the reaction space (1200) or the separation unit (1210). The reaction space may be followed, if required, by an apparatus for cleavage of carbamoyl chloride (not shown in FIG. 1). In such a case, the liquid phase (60) passes through this apparatus before it is subjected to the workup in step B. The resultant hydrogen chloride-enriched gas phase is preferably combined with the gas phase (70) and they are subjected to further workup together.

In this embodiment, this workup in step B comprises at least step II):
  II) depleting phosgene and hydrogen chloride from the liquid stream (60) from step I) by separating this liquid stream (60) into a liquid stream (80) comprising solvent and isocyanate, and a gaseous stream (90) comprising phosgene and hydrogen chloride in a distillation apparatus (2100; "dephosgenation column").

The further removal of hydrogen chloride and phosgene from the liquid crude isocyanate stream 60 in what is called the dephosgenation column 2100 in B.II) can be effected by any desired process known from the prior art, preferably as described in EP 1 854 783 B1, especially in paragraphs [0018] and [0023].

In steps I) and II) described, the gaseous streams (70) and (90) are obtained. These, preferably after passing through further cleaning steps, are sent to step a) as a constituent, if appropriate as the sole constituent, of the at least one solvent-containing offgas stream. In such further cleaning steps, the composition of streams (70) and (90) is altered (for example, these streams may be depleted of phosgene, hydrogen chloride and/or solvent).

In addition to the gaseous streams (70) and (90) mentioned, gaseous streams may be obtained at other points in the process, and become part of the workup of the gaseous process products in the process of the invention for preparation of an isocyanate in the manner outlined. One example of this is gaseous streams that result in the further separation of solvent from stream (80) via stream (130). This is preferably accomplished in such a way that step B.II) is followed by:
  III) depleting solvent from the liquid stream (80) from step II) by separating this liquid stream (80) into a gaseous stream (110) comprising solvent, and a liquid stream (100) comprising isocyanate in a distillation apparatus (2200; "solvent column");
  IV) depleting phosgene from the gaseous stream (110) from step IV) by separating this gaseous stream (110), preferably after its liquefaction in a condenser (2310), into a liquid stream (120) comprising solvent and a gaseous stream (130) comprising phosgene in a distillation apparatus (2300; "solvent stripper").

Step B.III) can be effected by any process known from the prior art, preferably as described in EP 1 854 783 B1, especially in paragraphs [0024] to [0027]. The distillation apparatus (2200) may also comprise two or more distillation columns connected in series (this option is not shown in FIG. 1 for reasons of simplification of the drawing).

Step B.IV) can be effected by any process known from the prior art, preferably as described in EP 1 854 783 B1, especially in paragraphs [0027] and [0028].

In step B.IV), the gaseous stream (130), is obtained. These, preferably after passing through further cleaning steps, are sent to step a) as a constituent of the at least one solvent-containing offgas stream. In this regard, reference may be made to the remarks relating to the gaseous streams (70) and (90).

The further cleaning steps of gas streams (70), (90) and (130) prior to performance of step a) that have been mentioned may be configured in various ways. In a preferred embodiment of the process of the invention, step B additionally comprises step VI):
  VI) cleaning (i.e. substantially freeing of phosgene) the gaseous streams (70) and (90) and, if present, the gaseous stream (130) by absorption in solvent (4) to obtain a liquid stream (160) comprising solvent and phosgene, and a gaseous stream (170) comprising hydrogen chloride and solvent in an absorption apparatus (2500; "phosgene absorber"), wherein preferably the gaseous streams (70) and (90) are first combined and the combined stream of (70) and (90), and also, if present, stream (130), are each condensed and then introduced in liquid form into the absorption apparatus (2500).

Step VI) can be effected by any process known from the prior art, preferably as described in EP 2 093 215 A1.

Stream (170) formed in step VI) can in principle be sent to step a). However, it is preferable to further purify the gaseous stream (170) beforehand. This encompasses a depletion of the hydrogen chloride content in a step VII):

VII) cleaning the gaseous stream (170) in water or hydrochloric acid as absorbent (180) in a further absorption apparatus (2600; "HCl absorption column") to obtain a hydrochloric acid-containing stream—optionally with traces of solvent—(190) and, preferably after passing through a vapor condenser (2610), a gaseous stream (200) comprising solvent and optionally gaseous secondary components.

Step VII) can be effected by any process known from the prior art. Preference is given to procedures as described in EP 2 021 275 B1.

The absorbent (180) used is water (e.g. steam condensate) or hydrochloric acid in a concentration in the range from 0.50% by mass to 15.0% by mass (dilute hydrochloric acid). The hydrochloric acid-containing stream (190) is discharged into the hydrochloric acid tank (2630). As well as the hydrochloric acid tank (2630), a further storage tank (2640) is disposed such that it can accept stream (190) if required. This "dilute acid tank" (2640) is utilized when the composition of the stream (190) differs significantly from the specification required for hydrochloric acid.

The heat released in the absorption of the hydrogen chloride transfers solvent present in stream (170) predominantly or completely to the gas stream (200).

In the preferred embodiment using the vapor condenser (2610), a liquid stream (191) is obtained therein. The stream (191) generally contains aqueous and organic constituents. In this embodiment, it may therefore be appropriate to separate stream (191) in a phase separation apparatus (2620) into an aqueous phase (192) and an organic phase (193). The aqueous phase (192) is preferably—especially preferably after discharge into the dilute acid tank (2640)—recycled into the HCl absorption column (2600) as a constituent of the absorbent (180). For further use, the water-saturated organic phase (193) is collected in a reservoir vessel (2710) and, preferably after drying (especially by means of molecular sieves in a drying vessel 2710), recycled into at least one of steps A.I) and B.III). This can be accomplished by admixing fresh solvent (4) which is used in A.I) with the organic phase (193) after drying or guiding it directly into the solvent tank (1040). It is also possible to introduce the organic phase (193), preferably after drying, into the distillation column (2200), for example by mixing it with stream (80) or, as shown in FIG. 1, introducing it into this distillation column independently of stream (80), and in this way guiding it via streams (110) [from the distillation apparatus (2200), B.III)] and (120) [(from the distillation apparatus (2300), B.IV)] into the solvent tank (1040). It is also possible to use (B-VI) the organic phase (193), after drying, as a constituent of the solvent (4) used in the absorption apparatus (2500).

The absorption process in step VII) can also be combined with direct or indirect stripping in order to ensure that the solvent content in stream (190) is at a minimum.

The preferred use—especially in the case of additional stripping—of the vapor condenser (2610) which is operated with cooling water at temperatures in the range from 0.5° C. to 60.0° C., preferably 10.0° C. to 30.0° C., offers a simple means of condensing the gaseous top stream from column (2600) as far as possible with acceptable expenditure. A suitable choice of the condensation temperature can additionally be one of the factors that affects the proportions in which solvent condenses out at this point in the process or is recycled into step a).

Figure 2:
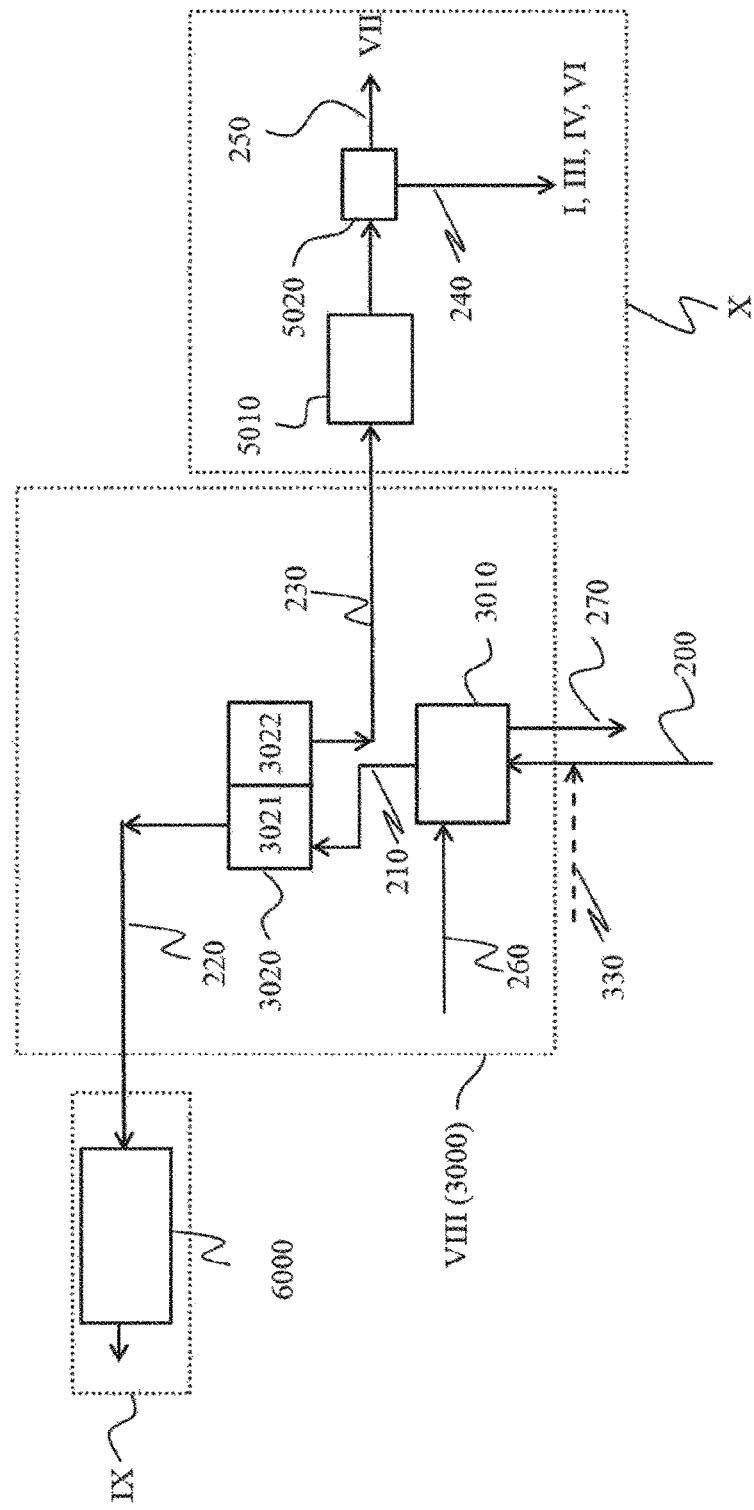
FIG. 2 is a detailed schematic diagram of components VIII), IX) and X) of a plant for preparation of an isocyanate by phosgenation of the corresponding amine.

The gaseous stream (200) can in principle be sent to step a). However, it is preferable to further purify this stream beforehand and more particularly to break down residues of phosgene that have not been separated out as yet. For this purpose, in a preferred embodiment, this is followed by step B.VII):

VIII) cleaning the gaseous stream (200) comprising solvent and optionally gaseous secondary components in an apparatus for workup of offgas streams (3000), where (see FIG. 2 for details)

VIII-1) the gaseous stream (200) that originates from the adsorption apparatus (2600), preferably after passing through the vapor condenser (2610), is guided into an apparatus for phosgene decomposition (3010; "phosgene destruction") in which phosgene is broken down catalytically, preferably over activated carbon, using water (260) to obtain a gaseous stream (210) comprising solvent and optionally gaseous secondary components and a liquid stream (270) comprising hydrochloric acid, wherein the gaseous stream (210) is guided into the adsorption apparatus (3020) for adsorption of solvent in step a).

The apparatus for decomposition of phosgene (3010) is preferably operated in such a way that phosgene is broken down catalytically, preferably over activated carbon, using water at a temperature in the range from 5.0° C. to 50.0° C., preferably 20.0° C. to 40.0° C. The cold water may be service water, steam condensate, demineralized water or a mixture of at least two of these. The use of steam condensate is preferred. The phosgene decomposition is preferably effected at a pressure in the range from 800 mbar to 1000 mbar (absolute), preferably 850 mbar to 950 mbar (absolute), especially in two tubular reactors connected in series ("phosgene destruction towers").

In this embodiment of the invention, the stream to be fed to the adsorption apparatus (3020) in step a) thus comprises the virtually phosgene-free gaseous stream (210) comprising solvent and any gaseous secondary components (other than phosgene) which is obtained in the phosgene decomposition (3010). The stream to be fed to step a) may also consist exclusively of this gaseous stream (210).

The apparatus for adsorption of solvent (3020) is preferably operated in such a way that the at least one solvent-containing offgas stream, i.e. especially stream (210), is passed over activated carbon at a temperature in the range from 20.0° C. to 60.0° C., preferably 30.0° C. to 45.0° C., and a pressure in the range from 850 mbar to 1000 mbar (absolute), preferably 920 mbar to 980 mbar (absolute), where the solvent is adsorbed on the activated carbon in the adsorption unit (3021) to such an extent that the saturation limit of the activated carbon is not exceeded. By contrast with the phosgene decomposition in (3010), no water is added in (3020). After such a loading interval has ended, the activated carbon in the unit (3021) is then regenerated by desorbing the solvent adsorbed on the activated carbon from the activated carbon again by direct introduction of steam (process stage a) (ii)). The resultant hot, aqueous solvent mixture (230) is cooled down in a condenser (5010) and separated in a phase separation apparatus (5020) into an aqueous phase (250), which is guided into the "dilute acid tank" (2640), and into an organic phase (240) comprising the solvent, which is guided into the storage vessel (2700). The length of a loading interval in terms of time depends on the solvent concentration in the at least one solvent-containing offgas stream, i.e. stream (210) in particular, and the available volume of activated carbon. The solvent-depleted offgas stream (220) to be fed to the offgas combustion (6000) is monitored for organic carbon at intervals or continuously, preferably continuously, with an analyzer. The duration of a loading interval is chosen such that there are no unwanted losses of solvent via the combustion. In order to be able to operate a continuous offgas cleaning operation, during the regeneration of the activated carbon in the adsorption unit (3021), the at least one solvent-containing offgas stream, i.e. offgas stream (210) in particular, is guided through a second, identical adsorption unit (3021) and depleted of solvent therein. A loading interval has a length of preferably 1.0 hour to 24 hours, more preferably 1.5 hours to 12 hours and most preferably 2.0 to 6.0 hours.

The solvent-depleted offgas stream (220) from the absorption apparatus (3020) which is obtained in step a) (i) is sent to the combustion (6000). The stream (230) comprising water and solvent which is obtained in step a) (ii) is (see FIG. 2)

X) preferably depleted of water in such a way that this stream (230) is condensed in a condenser (5010) and then separated in a phase separation apparatus (5020) into an aqueous phase (250) and an organic phase (240), where the organic phase (240) may optionally be dried further. The organic phase that has optionally been dried further is then recycled into at least one of steps A.I), B.III), B.IV) and B.VI). The aqueous phase (250) can advantageously be used as a constituent of the absorbent used in step VII); for intermediate storage, the aqueous phase (250) is preferably guided into the "dilute acid tank" (2640).

The preferred drying of the organic phase (240) can be effected, for example, by drying over zeolites. Suitable zeolites are, for example, molecular sieves having a pore size of 2.0 Å to 10 Å, preferably 3.0 Å to 5.0 Å.

Fresh solvent (4) which is used in A.I) can be admixed with the organic phase (240) after drying or it can be guided directly into the solvent tank (1040). The optionally dried organic phase (240) can likewise be introduced into the distillation column (2200), for example by mixing it with stream (80) or introducing it into this distillation column independently of stream (80), and in this way it can be guided via streams (110) [from the distillation apparatus (2200), B.III)] and (120) [(from the distillation apparatus (2300), B.IV)] into the solvent tank (1040). It is also possible to use optionally dried organic phase (240) as a constituent of the solvent (4) used as absorbent in the absorption apparatus (2500).

For safety reasons, in all embodiments of the invention, it is preferable to prepare the phosgene (3) required for the performance of step A on site by reaction of carbon monoxide (300) with chlorine (310) in a corresponding apparatus (4000). For the execution of this step, it is possible to utilize a "low-temperature combiner" according to EP 1 640 341 B1 or a "high-temperature combiner" according to EP 0 134 506 B1. High-temperature combination (see EP 0 134 506 B1)—which is used with preference—involves converting phosgene by reaction of chlorine with carbon monoxide in tubular reactors containing activated carbon as catalyst with simultaneous exploitation of the heat of reaction obtained for generation of steam. This is done by reacting, in a first tubular reactor containing granular activated carbon and having a clear tubular diameter of not more than 100 mm, 95% by volume to 98% by volume of the chlorine used with excess carbon monoxide to give phosgene at reaction temperatures exceeding 250.0° C. The heat of reaction obtained here is removed by evaporative cooling of a liquid that boils at 150.0° C. to 320.0° C. or with a non-boiling liquid, the temperature of which is kept at 150.0° C. to 320.0° C. at the reactor outlet by means of forced circulation pumps and temperature control. The liquid or vaporous heat carrier leaving the reactor is condensed in a heat exchanger charged with water as cooling medium to generate steam and/or cooled to a temperature below the temperature of the heat carrier at the reactor exit and recycled into the reactor. The reaction gases leaving the reactor are cooled to a temperature of 50.0° C. to 120.0° C. and then passed into a second reactor containing granular activated carbon, the temperature of which is set to 50.0° C. to 100.0° C. by thermostatic means and in which the conversion is conducted to completion, such that the phosgene leaving the second reactor has a residual chlorine content of less than 50 ppmv. The phosgene exiting at the top of the reactor is condensed as described above. In every process, an offgas stream (320) comprising carbon monoxide and residues of phosgene arises, which, preferably after passing through further cleaning steps, is fed into the at least one solvent-containing offgas stream from step a) which is to be sent to the offgas combustion (6000). Suitable cleaning steps include an absorption of the offgas stream (320) in solvent (4) having a temperature in the range from 0.0° C. to −20.0° C. in an absorption column ("phosgene scrubber"; (4010)), wherein some of the phosgene is scrubbed out of the offgas stream (320) comprising carbon monoxide and residues of phosgene. The solvent- and phosgene-containing stream (340) obtained in the absorption column (4010) is preferably sent to the absorption apparatus (2500). The phosgene-depleted residual offgas stream (330) that still contains traces of solvent is preferably, as shown in FIG. 1, sent to the phosgene decomposition (3010). In this way, the offgas stream from the phosgene preparation is likewise sent to the adsorption of the invention.

For preparation of the desired isocyanate (1) in pure form, it is preferable to further distill the stream (100) obtained after removal of the solvent in the above-described solvent column (2200). This is preferably accomplished in a step B.V):

V) obtaining a liquid isocyanate stream (140) from the liquid stream (100), resulting in a gaseous stream (150) comprising secondary components and optionally solvent, in a distillation apparatus (2400), optionally comprising the removal of polymeric isocyanate fractions in an upstream unit for polymer removal (2410) as stream (141).

In this embodiment, stream (140) thus comprises the isocyanate (1) in a purified form. In this context, (140) may also cumulatively represent different isocyanate streams (1) of different isomer composition (140-1, 140-2, . . . ), if the distillation in 2400 includes not just a cleaning operation but also an isomer separation. In addition, the stream 141 obtained in particular embodiments also contains isocyanates (1), where stream 141 comprises, in particular, polymeric isocyanate fractions (i.e. isocyanates (1) that can be derived from polymerized amines, for example polymethylene polyphenylene polyisocyanates having three or more benzene "nuclei"). The "residue stream" 143 obtained in the particular embodiments—i.e. particularly without the upstream polymer removal in 2410—also still contains isocyanate (1), which can be obtained from this stream. The latter embodiment is particularly suitable for the preparation of tolylene diisocyanate, in which case the distillation apparatus 2400 is preferably configured as a dividing wall column.

Step V) can be effected by any process known from the prior art. Suitable processes are described in EP1475367B1, or else in EP 1 371 635 B1.

In the process according to the invention, in particular, units in process steps III), IV) and V) [(i.e. (2200), (2300), if present (2410) and (2400)] are operated at a reduced pressure relative to atmospheric pressure. The vacuum generation plants required for this purpose produce offgas streams (not shown in FIG. 1). In the prior art, these offgas streams are typically, preferably after purification, partially condensed at comparatively low temperature (−30.0° C. to 0.0° C.) in order to condense out entrained solvent. The process of the invention makes it possible to perform this condensation at higher temperature (1.0° C. to 50.0° C.; saving of refrigeration energy) or even to dispense with this condensation entirely. It is also possible (and preferable) in accordance with the invention, rather than said condensation, to conduct a simple liquid separation (droplet separation). Suitable units for this purpose are known to those skilled in the art and include, preferably, gravitational separators, cyclones, lamella separators, knits and the like. The offgas from the vacuum generation plants that has been freed of entrained liquid by condensation at comparatively high temperature or liquid separation and is obtained in this way can in principle be sent directly to step a). However, it is preferable to further purify this stream, just like stream (200) previously, and especially to break down traces of phosgene. For this purpose, the offgas from the vacuum generation plants that has been freed of entrained liquid is cleaned in the apparatus for workup of offgas streams (3000), wherein the offgas streams, just like stream (200), are first guided into an apparatus for phosgene decomposition (3010; "phosgene destruction") and then fed as a constituent of the gaseous stream (210) into the adsorption apparatus (3020) for adsorption of solvent from step a).

The present invention further provides a plant (10 000) for preparing an isocyanate (1) by phosgenation of the corresponding amine (2), comprising the following plant components:

0) optionally and preferably an apparatus (4000) for production of phosgene (3) by reaction of carbon monoxide (300) with chlorine (310), giving an offgas stream (320) comprising carbon monoxide and phosgene;

I) a reaction zone (1000) comprising a reaction space (1200) for performance of the phosgenation, with a separation unit (1210) optionally connected downstream, where the reaction space or the separation unit have been provided with outlet conduits for a liquid stream (60) and a gaseous stream (70);

II) a distillation apparatus (2100) for separating the liquid stream (60) into a liquid stream (80) and a gaseous stream (90);

III) optionally and preferably a distillation apparatus (2200) for separating the liquid stream (80) into a gaseous stream (110) and a liquid stream (100);

IV) optionally and preferably a distillation apparatus (2300) for separating the gaseous stream (110), preferably after its liquefaction in a condenser (2310), into a liquid stream (120) and a gaseous stream (130);

V) optionally and preferably a distillation apparatus (2400) for obtaining a liquid isocyanate stream (140) from the liquid stream (100), resulting in a gaseous stream (150) comprising secondary components and optionally solvent, optionally comprising an upstream unit for polymer removal (2410) for removal of polymeric isocyanate fractions (141);

VI) an apparatus for absorption (2500) of the gaseous streams (70) and (90) and, if present, of the gaseous stream (130), optionally after passing through units (2510) for condensation (not shown in FIG. 1) connected upstream of the apparatus for absorption (2500), in solvent (4) to obtain a liquid stream (160) and a gaseous stream (170);

VII) an apparatus for absorption (2600) of the gaseous stream (170) in water or hydrochloric acid, preferably comprising a vapor condenser (2610), to obtain a stream (190) comprising hydrochloric acid and a gaseous stream (200) comprising solvent and optionally gaseous secondary components;

VIII) an apparatus for workup of offgas streams (3000), comprising

VIII-1) an apparatus for catalytic phosgene decomposition (3010) for the decomposition of phosgene present in stream (200) and preferably also the decomposition of phosgene present in stream (320) to obtain a gaseous stream (210) comprising solvent and optionally gaseous secondary components;

VIII-2) an adsorption apparatus (3020) for adsorption of solvent from stream (210), wherein the adsorption apparatus (3010) comprises at least two adsorption units (3021, 3022) connected in parallel, which are configured such that they can alternately be
(i) charged with stream (210) and
(ii) regenerated with steam;

IX) an apparatus for offgas combustion (6000) for combustion of the gas stream (220) obtained in VIII-2) (i);

X) units for recycling of solvent desorbed in process stage VIII-2) (ii) into the reaction zone (1000) and/or into the apparatus for absorption (2500).

The process of the invention gives rise at least to the following advantages:

i) Solvent can be recovered from the offgas stream to be sent to the combustion without energy-intensive cooling to very low temperatures (<−30.0° C.). There are no maintenance costs for refrigeration.

ii) Minimization of the solvent content combusted in the offgas combustion, hence minimization of combustion residues. Since solvents used in isocyanate preparation frequently contain chlorine, it is additionally possible to simplify the cleaning of combustion offgases.

iii) The recovery of the solvent drastically reduces the buying-in of fresh solvent, hence sparing of resources.

iv) Dispensing with electrical trace heating in the offgas conduit between phosgene decomposition and waste air combustion and a liquid separator in the offgas conduit.

The success of the procedure of the invention for solvent recovery through use of a downstream solvent adsorption plant compared to a pure thermal utilization of the solvent in the combustion was surprising to the person skilled in the art in spite of the capital costs for an additional adsorption stage. A production plant with solvent adsorption can be operated with low steam consumption and very low maintenance expenditure (exchange of the activated carbon for the adsorption frequently required only after five years).

The present invention is to be illustrated further hereinafter by specific examples.

EXAMPLES

General Conditions for the Preparation of a Mixture of Methylene Diphenylene Diisocyanate and Polymethylene Polyphenylene Polyisocyanate (Collectively MDI Hereinafter) in Regular Operation—Process Stages I to IX; Cf. Also FIG. 1

20.4 t/h of a mixture of methylene diphenylene diamine and polymethylene polyphenylene polyamine (collectively MDA hereinafter; 2) at a temperature of 110.0° C. are mixed with 55.0 t/h of monochlorobenzene (MCB; 4) at a temperature of 30.0° C. as solvent by means of a static mixer (1020) to give a 27.1% MDA solution (20). Phosgene (3) is provided by means of an apparatus for production of phosgene (4000), comprising two phosgene generators and two phosgene liquefiers (see the description of process stage 0 further down). Thereafter, the phosgene (3) is mixed in a phosgene solution tank (1030) with stream 160 consisting predominantly of MCB (4) to give a 35.0% phosgene solution (30). 120 tonnes per hour of this phosgene solution (30) at a temperature of 0.0° C. are reacted with 20.4 tonnes per hour of 27.1% MDA solution (20) at a temperature of 45.0° C. in an adiabatic reaction, as described in EP 1 873 142 B1. After the two raw material solutions have been mixed in the mixing apparatus (1100), the reaction solution (50) obtained is run at a temperature of 81.0° C. through a pipeline ("suspension conduit") into a heated phosgenation tower (1200). At the top of the phosgenation tower, the absolute pressure is 1.6 bar and the temperature is 111.0° C. The hydrogen chloride formed in the reaction is removed together with traces of phosgene and MCB as gas stream (70). The liquid reaction mixture (60) is withdrawn from the phosgenation tower (1200) and fed to the workup sequence (II ff.). For this purpose, it is first introduced as a sidestream into a heated dephosgenation column (2100, II). At a top temperature of 116.0° C. and an absolute pressure of 1.6 bar, phosgene is removed overhead (90) together with traces of MCB and hydrogen chloride. Phosgene is absorbed in the MCB in a phosgene absorption column (2500, VI), and the phosgene solution obtained is run into the phosgene solution tank (1030). Hydrogen chloride is guided into a hydrogen chloride absorber (2600, VII); the hydrochloric acid obtained therein is guided into the hydrochloric acid tank (2630) for further use. The vapors from the hydrogen chloride absorption (2600) are partially liquefied in the condenser 2610; the remaining gas stream (200) is sent to the apparatus for workup of offgas streams (3000, VIII), comprising at least one phosgene decomposition (3010) as the first unit in flow direction. The offgas pathway proceeding from the gaseous phase of the phosgene absorption column (2500, VI) into the hydrogen chloride absorption (2600, VII) and thence via the gaseous phase into the apparatus for workup of offgas streams (3000, VIII) as far as the offgas combustion (6000, IX) has been opened.

After removal of hydrogen chloride and excess phosgene from the isocyanate-containing reaction solution (60), a crude isocyanate solution (80) is obtained, which is discharged from the bottom of the dephosgenation column 2100 and run at a temperature of 155.0° C. into a first distillation stage of the solvent distillation (2200, III), in order to free it of the MCB solvent. The absolute pressure at the top of this solvent distillation column (2200) is 600 mbar at a bottom temperature of 145.0° C. MCB is drawn off in gaseous form overhead (110), and this MCB gas stream is condensed in an air condenser (2310). 18.0 t/h of this condensed solvent are sprayed into a scrubbing column (not shown in FIG. 1), in order to prevent any possible entrainment of isocyanate into the vacuum conduits. The remaining condensed MCB (100 t/h) is pumped to a distillation column (2300, IV) in which the MCB is freed of phosgene, and the phosgene-containing vapors (130) are condensed and pumped into the phosgene absorber (2500, VI), and the phosgene-free MCB from the bottom of the solvent stripper (120) is pumped into the solvent tank (1040). The crude MDI is discharged from the bottom of the column 2200 and freed of the residual MCB down to 1% in a second distillation column (not shown in FIG. 1). The absolute pressure at the top of this solvent distillation column is 70 mbar at a bottom temperature of 150.0° C. MCB is drawn off in gaseous form overhead, and this MCB gas stream is condensed and recycled into the bottom of the first distillation column (2200). Subsequently, in a countercurrent evaporator, at an absolute pressure of 20 mbar and a top temperature of 170.0° C., the product is freed of secondary components such as phenyl isocyanate and residual MCB. 25.45 t/h of MDI are obtained as bottom product (100), which are separated by means of further distillation steps (2410/2400) into methylene diphenyl diisocyanate (140) and a mixture of methylene diphenyl diisocyanate and polymethylene polyphenyl polyisocyanate (141).

General Conditions for the Preparation of Phosgene—Process Stage 0

In a mixing tube, 4400 $m^3$ (STP)/h of chlorine and 4650 $m^3$ (STP)/h of carbon monoxide are mixed continuously at 18.0° C. and a pressure of 1.8 bar (absolute). An excess of carbon monoxide is used relative to chlorine, such that, after the complete reaction of the chlorine, there is still 9.0% carbon monoxide remaining in the phosgene. The mixed gas composed of chlorine and carbon monoxide is run in to a distributor present at the base of a shell and tube phosgene generator. There are 10 tonnes of activated carbon (Norit RB4C) present as catalyst in the tubes above the distributor. Over this catalyst, the mixed gas is depleted in a highly exothermic reaction to give phosgene. The reaction is cooled via water circulation by means of evaporative water cooling. The temperature of the phosgene in the exit line of the generator is 55.0° C. and the pressure is 1.53 bar (absolute). At this point, the completeness of the reaction is monitored by continuously measuring the residual chlorine content and the carbon monoxide content. The gaseous phosgene containing excess carbon monoxide which is prepared in this way is then condensed in a phosgene liquefier at −17.0° C. The bottom product from the phosgene liquefier runs into a phosgene solution tank (1030). Excess carbon monoxide does not condense and is run overhead into a downstream second phosgene generator of identical design, where it is contacted with an appropriate amount of chlorine, such that, after complete conversion of the chlorine, there is again still 9.0% of carbon monoxide remaining in the phosgene. Downstream of the second phosgene generator as well, the completeness of the reaction is monitored by continuously measuring the residual chlorine content and the carbon monoxide content. The phosgene thus prepared is condensed in a second phosgene liquefier at −17.0° C. The bottom product from the second phosgene liquefier likewise runs into the phosgene solution tank. Thus, 42 tonnes of phosgene per hour arrive in the phosgene solution tank.

As the top product (stream 320) from the phosgene liquefier, 150 $m^3$/h of excess carbon monoxide also contaminated with traces of phosgene (0.50% of the total amount of offgas) are subjected to preliminary cleaning in an absorption column ("phosgene scrubber" (4010)) which is operated with cold solvent (MCB) at −17.0° C., scrubbing some of the phosgene out of the gas stream. The phosgene-containing MCB solution thus obtained is sent to the phosgene absorption (2500) as liquid stream (340). The remaining offgas stream (330) still contaminated with traces of solvent and phosgene is combined with stream (200) and sent to the phosgene decomposition (3010).

In the phosgene solution tank (1030), the phosgene can, if required, be mixed with further solvent (4) (solvent is always present in the phosgene solution tank via stream 160).

What are called ammonia screw compressors are used for refrigeration in the phosgene liquefiers. In this way, the MCB solvent that finds use in the reaction and the MCB coolant with which the coolers for the condensation of the offgas streams are supplied are cooled down to −17.0° C.

Example 1 (Comparative Example): Partial Recovery of the Solvent Using MCB at a Temperature of −17.0° C. for the Condensation of the Offgas from the Vacuum Generation The plants for preparation of phosgene and for preparation of MDI were operated at nameplate load as described in the two sets of general preparation conditions. All offgas streams from the two plants comprised entrained MCB. The offgas streams were composed of the offgases from the phosgene preparation in process stage 0) (150 m³/h), from the vacuum generation for the distillation in process step V) (50 m³/h), and from the hydrogen chloride absorption in process stage VII) (100 m³/h). The offgas from the vacuum generation (not shown in the drawings) by the vacuum pumps and their reservoirs in the MDI plant in process steps III, IV and V was combined and sent to the phosgene decomposition (3010) via a condenser that was operated with MCB at a temperature of −17.0° C. The offgas stream (170) from the phosgene absorption (7500 m³/h) was guided into the hydrogen chloride absorber (2600). The procedure for the recovery of the MCB solvent present in the offgas streams was as follows. The 150 m³/h of the offgas stream (330) from the phosgene scrubber (4010) in the phosgene plant were combined with the 100 m³/h of the offgas stream (200) from the condenser in the hydrogen chloride absorption (2610) in the MDI plant, and sent to the phosgene decomposition (3010). The combined offgas was run through the phosgene decomposition by means of a ventilator mounted behind it. At nameplate load, a total of 300 m³/h of offgas were run into the phosgene decomposition (3010). The two phosgene destruction towers connected in series, each of which was charged with 14 m³ of Norit RB4C activated carbon, were operated at a reduced pressure of 930 mbar absolute. The phosgene decomposition was operated with a circulation of cold condensate at 25.0° C. (stream 260), which kept the activated carbon permanently wet and scrubbed out dilute hydrochloric acid (stream 270) that was run into the dilute acid tank (2640). The offgas stream (210) of 300 m³/h that left the phosgene decomposition was sent to the combustion (6000). The offgas conduit between phosgene decomposition and the offgas combustion is trace-heated in order to minimize condensation of MCB. In addition, a liquid separator is incorporated into this offgas conduit in order to discharge condensed, water-moist, acidic MCB.

Overall Assessment:

In this way, a total of 330 tonnes of solvent per year were lost via the offgas combustion in 8000 hours of operation, and a further 100 tonnes of solvent per year that had to be discharged from the liquid separator had to be combusted separately. For the refrigeration energy for condensation of the solvent out of the offgas from the vacuum generation, 103 kWh were required.

Example 2 (Inventive): Recovery of the Solvent by Means of an Apparatus for Solvent Adsorption without Use of MCB at a Temperature of −17.0° C. for Condensation of MCB in the Offgas The plants for preparation of phosgene and for preparation of MDI were operated at nameplate load as described in the two sets of general preparation conditions. All offgas streams from the two plants comprised entrained MCB. The offgas streams were composed of the offgases from the phosgene preparation in process stage 0) (150 m³/h), from the vacuum generation for the distillation in process step V) (50 m³/h), and from the hydrogen chloride absorption in process stage VII) (100 m³/h). The offgas streams from the vacuum generation (not shown in the drawings) by the vacuum pumps and their reservoirs in process steps III, IV and V were combined and sent to the phosgene decomposition (3010) at 29.0° C. via a liquid separator (in which MCB- and phosgene-containing droplets that were entrained in the offgas were separated out by gravity). The offgas stream (170) from the phosgene absorption (9000 m³/h) was guided into the hydrogen chloride absorber (2600). The procedure for the recovery of the MCB solvent present in the offgas streams was as follows. The 150 m³/h of the offgas stream (330) from the phosgene scrubber (4010) in the phosgene plant were combined with the 100 m³/h of the offgas stream (200) from the condenser in the hydrogen chloride absorption (2610) in the MDI plant, and sent to the phosgene decomposition (3010). The combined offgas was run through the phosgene decomposition by means of a ventilator mounted behind it. At nameplate load, a total of 300 m³/h of offgas were run into the phosgene decomposition (3010). The two phosgene destruction towers connected in series, each of which was charged with 14 m³ of Norit RB4C activated carbon, were operated at a reduced pressure of 900 mbar absolute. The phosgene decomposition was operated with a circulation of cold condensate at 25.0° C. (stream 260), which kept the activated carbon permanently wet and scrubbed out dilute hydrochloric acid (stream 270) that was run into the dilute acid tank (2640). The offgas stream (210) of 300 m³/h that left the phosgene decomposition was guided through the solvent adsorption (3020).

The solvent adsorption was operated in such a way that the solvent-containing offgas from stream (210) at 47.0° C. was guided through 2 m³ of Norit RB4C activated carbon, with adsorption of the solvent on the activated carbon at 950 mbar absolute. The offgas stream (220) was monitored continuously for organic carbon with an analyzer (FID). The loading interval was synchronized such that there were no losses of solvent. In order to avoid solvent losses as a result of saturation of the activated carbon with solvent via the offgas stream (220), after a loading interval of two hours, the activated carbon was regenerated for one hour. During this period, the solvent adsorption was continued by means of a solvent adsorption of identical construction that was connected in parallel. The regeneration of the activated carbon was conducted in such a way that the solvent adsorbed on the activated carbon was desorbed with 0.15 tonne of direct 2.5 bar steam for one hour. The resultant hot, aqueous solvent mixture (230) was cooled to 30.0° C. by means of a condenser (5010) that was operated with cooling water, and separated in a solvent separator (5020) into an aqueous phase (250) that was guided into the dilute acid tank (2640) and an organic phase (240) containing the water-saturated MCB solvent that was guided into a reservoir vessel (2700) at 100 kg/h. The solvent drying was put into operation twice per week in batchwise mode. The drying was effected with a molecular sieve having a pore size of 4 Å. For this purpose, 5 tonnes of moist MCB solvent were guided with a pump from the reservoir vessel (2700) through a drying vessel (2710) filled with 50 kg of the molecular sieve from the bottom upward for 15 hours. The MCB leaving the drying vessel still had a residual moisture content of 40 ppm and was recycled into the solvent distillation (2200). The molecular sieve was then regenerated with 20 m$^3$/h of nitrogen at a temperature of 80.0° C. over two days. The nitrogen was heated up by means of a heat exchanger with 2.5 bar of excess, internally raised steam.

Overall Assessment:

In this way, a total of 30 tonnes of solvent per year were lost in 8000 hours of operation. No refrigeration energy for condensation of the solvent out of the offgas from the vacuum generation was required. 20 000 m$^3$/a of hot nitrogen were consumed for the regeneration of the molecular sieve from the solvent drying, which was heated with excess internally raised 2.5 bar steam. The molecular sieve has to be replaced once per year. For the regeneration of the activated carbon in the solvent adsorption, 600 to/a of excess, internally raised 2.5 bar steam were consumed. The activated carbon in the solvent adsorption has to be replaced every 5 years.

Conclusion:

Overall, the invention saved 400 tonnes of MCB and 828 KW of refrigeration energy. On the other hand, there is additional expenditure on apparatuses (solvent adsorption, solvent condenser, solvent separator, solvent drying, reservoirs and pipelines) and for the auxiliary nitrogen. However, the operation of these additional units is afflicted with only extremely low capital costs and maintenance costs. The costs for molecular sieve and activated carbon and nitrogen are low. The steam required is internally raised excess steam that would otherwise have to be condensed by means of an air cooler and sent to further condensate processing.

The invention claimed is:

1. A process for preparing an isocyanate (1), comprising:
    A. reacting the amine (2) that corresponds to the isocyanate (1) with phosgene (3) using a solvent (4) to obtain a liquid stream comprising the isocyanate (1) and solvent (4) and at least one solvent-containing offgas stream; and
    B. working up the liquid stream comprising isocyanate and solvent to isolate the isocyanate, wherein further solvent (4) may be used, to obtain at least one solvent-containing offgas stream;
    wherein
    a) the at least one solvent-containing offgas stream from step A and/or from step B is guided into an adsorption apparatus for adsorption of solvent (3020) comprising at least two adsorption units (3021, 3022) connected in parallel that are alternately
        (i) charged with the at least one offgas stream to obtain a solvent-depleted offgas stream (220), and
        (ii) regenerated with steam to obtain a stream comprising water and solvent (230),
    b) (i) the solvent-depleted offgas stream (220) is sent to an offgas combustion (6000) and
        (ii) the stream comprising water and solvent (230) is depleted of water and then recycled into step A and/or into step B.

2. The process of claim 1, in which step A comprises:
    I) reacting the amine (2) with phosgene (3) and separating the process product obtained into the liquid stream (60) comprising the isocyanate and solvent, and a gaseous stream (70) comprising phosgene, hydrogen chloride and solvent;
    and in which step B comprises:
    II) depleting phosgene and hydrogen chloride from the liquid stream (60) from step I) by separating this liquid stream (60) into a liquid stream (80) comprising solvent and isocyanate, and a gaseous stream (90) comprising phosgene and hydrogen chloride in a distillation apparatus (2100);
    wherein the gaseous streams (70) and (90), optionally after passing through further cleaning steps, are sent to step a) as a constituent of the at least one solvent-containing offgas stream.

3. The process of claim 2, further comprising:
    III) depleting solvent from the liquid stream (80) from step II) by separating the liquid stream (80) into a gaseous stream (110) comprising solvent, and a liquid stream (100) comprising isocyanate in a distillation apparatus (2200);
    IV) depleting phosgene from the gaseous stream (110) from step IV) by separating the gaseous stream (110), optionally after its liquefaction in a condenser (2310), into a liquid stream (120) comprising solvent and a gaseous stream (130) comprising phosgene in a distillation apparatus (2300);
    wherein the gaseous stream (130), optionally after passing through further cleaning steps, is sent to step a) as a constituent of the at least one solvent-containing offgas stream.

4. The process of claim 3, further comprising:
    V) obtaining a liquid isocyanate stream (140) from the liquid stream (100), resulting in a gaseous stream (150) comprising secondary components and optionally solvent, in a distillation apparatus (2400), optionally comprising the removal of polymeric isocyanate fractions in an upstream unit for polymer removal (2410) as stream (141).

5. The process of claim 2, further comprising:
    VI) cleaning the gaseous streams (70) and (90) and, if present, the gaseous stream (130), optionally after condensation, by absorption in solvent (4) to obtain a liquid stream (160) comprising solvent and phosgene, and a gaseous stream (170) comprising hydrogen chloride and solvent in an absorption apparatus (2500).

6. The process of claim 5, further comprising:
    VII) cleaning the gaseous stream (170) in water or hydrochloric acid as absorbent (180) in a further absorption apparatus (2600) to obtain a hydrochloric acid-containing stream (190) and, optionally after passing through a vapor condenser (2610), a gaseous stream (200) comprising solvent and optionally gaseous secondary components.

7. The process of claim 6, in which step B.VII) includes passage through the vapor condenser (2610) and step B.VII) further comprises:
    separating the liquid stream (191) obtained in the vapor condenser (2610) into an aqueous phase (192) and an organic phase (193);

recycling the aqueous phase (192) as a constituent of the absorbent (180) into the absorption apparatus (2600) and/or recycling the organic phase (193), optionally after drying, into at least one of steps A.I), B.III), B.IV) and B.VI).

8. The process of claim 6, further comprising:

VIII) cleaning the gaseous stream (200) comprising solvent and optionally gaseous secondary components in an apparatus for workup of offgas streams (3000), wherein VIII-1) the gaseous stream (200) that originates from the absorption apparatus (2600), optionally after passing through the vapor condenser (2610), is guided into an apparatus for phosgene decomposition (3010) in which phosgene is decomposed catalytically using water (260) to obtain a gaseous stream (210) comprising solvent and optionally gaseous secondary components and a liquid stream (270) comprising hydrochloric acid, wherein the gaseous stream (210) is guided into the adsorption apparatus (3020) for adsorption of solvent in step a).

9. The process of claim 8, in which the phosgene (3) for the performance of step A is prepared by reacting carbon monoxide (300) with chlorine (310), giving an offgas stream (320) comprising carbon monoxide and phosgene which, optionally after passing through further cleaning steps, is fed into the at least one solvent-containing offgas stream to be sent to the offgas combustion.

10. The process of claim 9, in which the offgas stream (320) comprising carbon monoxide and phosgene from the reaction of carbon monoxide (300) with chlorine (310) is cleaned in solvent (4) having a temperature in the range from 0.0° C. to −20.0° C. in an absorption column (4010) to give a phosgene-depleted offgas stream (330) which, prior to performance of step VIII.1), is combined with the gaseous stream (200), giving a solvent- and phosgene-containing stream (340) in the absorption column (4010) which is sent to the absorption apparatus (2500).

11. The process of claim 1, in which the depletion of water from the stream comprising water and solvent in step b) (ii) is conducted in such a way that the stream is condensed and then separated into an aqueous phase (250) and an organic phase (240), wherein the organic phase (240) may optionally be dried further, and in which the recycling of the stream obtained after depletion of water into step A and/or into step B is conducted in such a way that the organic phase (240), optionally after further drying, is recycled into step A and/or into step B.

12. The process of claim 11, in which the aqueous phase (250) is used as a constituent of the absorbent used in step B.VII).

13. The process of claim 3, in which the units (2200) and (2300), and optionally additionally the units (2400) and, if present, (2410) are operated at a reduced pressure relative to atmospheric pressure and the offgas streams from the vacuum generation plants that are required for this purpose, are sent to step a) without cooling or after cooling to a temperature not lower than 1.0° C., optionally after passing through an apparatus for catalytic phosgene decomposition (3010).

14. The process of claim 1, in which the amine (2) is selected from the group consisting of methylene diphenylene diamine, polymethylene polyphenylene polyamine, a mixture of methylene diphenylene diamine and polymethylene polyphenylene polyamine, tolylenediamine, xylylenediamine, pentane-1,5-diamine, hexamethylenediamine, isophoronediamine and naphthyldiamine.

15. A plant (10 000) for preparation of an isocyanate (1) by phosgenation of the corresponding amine (2), comprising:

0) optionally an apparatus (4000) for production of phosgene (3) by reaction of carbon monoxide (300) with chlorine (310), giving an offgas stream (320) comprising carbon monoxide and phosgene;

I) a reaction zone (1000) comprising a reaction space (1200) for performance of the phosgenation, with a separation unit (1210) optionally connected downstream thereof, where the reaction space or the separation unit are provided with outlet conduits for a liquid stream (60) and a gaseous stream (70);

II) a distillation apparatus (2100) for separating the liquid stream (60) into a liquid stream (80) and a gaseous stream (90);

III) optionally a distillation apparatus (2200) for separating the liquid stream (80) into a gaseous stream (110) and a liquid stream (100);

IV) optionally a distillation apparatus (2300) for separating the gaseous stream (110), optionally after its liquefaction in a condenser (2310), into a liquid stream (120) and a gaseous stream (130);

V) optionally a distillation apparatus (2400) for obtaining a liquid isocyanate stream (140) from the liquid stream (100), resulting in a gaseous stream (150) comprising secondary components and optionally solvent, optionally comprising an upstream unit for polymer removal (2410) for removal of polymeric isocyanate fractions (141);

VI) an apparatus for absorption (2500) of the gaseous streams (70) and (90) and, if present, of the gaseous stream (130), optionally after passing through units (2510) for condensation connected upstream of the apparatus for absorption (2500), in solvent (4) to obtain a liquid stream (160) and a gaseous stream (170);

VII) an apparatus for absorption (2600) of the gaseous stream (170) in water or hydrochloric acid, optionally comprising a vapor condenser (2610), to obtain a stream (190) comprising hydrochloric acid and optionally solvent and a gaseous stream (200) comprising solvent and optionally gaseous secondary components;

VIII) an apparatus for workup of offgas streams (3000), comprising

VIII-1) an apparatus for catalytic phosgene decomposition (3010) for the decomposition of phosgene present in stream (200) and optionally also for the decomposition of phosgene present in stream (320) to obtain a gaseous stream (210) comprising solvent and optionally gaseous secondary components;

VIII-2) an adsorption apparatus (3020) for adsorption of solvent from stream (210), wherein the adsorption apparatus (3020) comprises at least two adsorption units (3021, 3022) connected in parallel, which are configured such that they can alternately be
(i) charged with stream (210) and
(ii) regenerated with steam;

IX) an apparatus for offgas combustion (6000) for combustion of the gas stream (220) obtained in VIII-2) (i); and X) units for recycling of solvent desorbed in process stage VIII-2) (ii) into the reaction zone (1000) and/or into the apparatus for absorption (2500).

* * * * *